(12) United States Patent
Bender et al.

(10) Patent No.: US 9,247,903 B2
(45) Date of Patent: Feb. 2, 2016

(54) USING AFFECT WITHIN A GAMING CONTEXT

(75) Inventors: Daniel Bender, Cambridge, MA (US); Rana el Kaliouby, Newtown, MA (US); Rosalind Wright Picard, Newtonville, MA (US); Richard Scott Sadowsky, Sturbridge, MA (US); Panu James Turcot, Cambridge, MA (US); Oliver Orion Wilder-Smith, Holliston, MA (US)

(73) Assignee: Affectiva, Inc., Waltham, MA (US)

( * ) Notice: Subject to any disclaimer, the term of this patent is extended or adjusted under 35 U.S.C. 154(b) by 0 days.

(21) Appl. No.: 13/366,648

(22) Filed: Feb. 6, 2012

(65) Prior Publication Data

US 2012/0135804 A1     May 31, 2012

Related U.S. Application Data

(63) Continuation-in-part of application No. 13/153,745, filed on Jun. 6, 2011, which is a continuation-in-part of application No. 13/297,342, filed on Nov. 16, 2011.

(60) Provisional application No. 61/439,913, filed on Feb.
(Continued)

(51) Int. Cl.
G06F 17/00     (2006.01)
A61B 5/16     (2006.01)
G06F 19/00     (2011.01)

(52) U.S. Cl.
CPC ............. *A61B 5/165* (2013.01); *G06F 19/3418* (2013.01)

(58) Field of Classification Search
CPC ............ G06F 17/00; G06F 19/00; A63F 9/24

USPC .............................................. 709/202; 463/36
See application file for complete search history.

(56) References Cited

U.S. PATENT DOCUMENTS

| 3,034,500 | A | 5/1962 | Backster, Jr. |
| 3,548,806 | A | 12/1970 | Fisher |
| 3,870,034 | A | 3/1975 | James |
| 4,353,375 | A | 10/1982 | Colburn et al. |
| 4,448,203 | A | 5/1984 | Williamson et al. |

(Continued)

FOREIGN PATENT DOCUMENTS

| JP | 08115367 | 7/1996 |
| KR | 10-2005-0021759 A | 3/2005 |

(Continued)

OTHER PUBLICATIONS

Rana Ayman El Kaliouby, Mind-reading machines: automated inference of complex mental states, Jul. 2005, University of Cambridge, Cambridge, United Kingdom.

(Continued)

*Primary Examiner* — Vivek Srivastava
*Assistant Examiner* — Sibte Bukhari
(74) *Attorney, Agent, or Firm* — Adams Intellex, PLC

(57) ABSTRACT

Mental state data is collected as a person interacts with a game machine. Analysis is performed on this data and mental state information and affect are shared across a social network. The affect of a person can be represented to the social network or gaming community in the form of an avatar. Recommendations can be based on the affect of the person. Mental states can be analyzed by web services which may, in turn, modify the game.

29 Claims, 8 Drawing Sheets

Related U.S. Application Data 6, 2011, provisional application No. 61/477,089, filed on Feb. 27, 2011, provisional application No. 61/477,464, filed on Feb. 28, 2011, provisional application No. 61/467,209, filed on Mar. 24, 2011, provisional application No. 61/549,560, filed on Oct. 20, 2011, provisional application No. 61/568,130, filed on Dec. 7, 2011, provisional application No. 61/580,880, filed on Dec. 28, 2011, provisional application No. 61/581,913, filed on Dec. 30, 2011, provisional application No. 61/352,166, filed on Jun. 7, 2010, provisional application No. 61/388,002, filed on Sep. 30, 2010, provisional application No. 61/414,451, filed on Nov. 17, 2010.

(56) References Cited

U.S. PATENT DOCUMENTS

| | | | |
|---|---|---|---|
| 4,683,891 A * | 8/1987 | Cornellier et al. | 600/301 |
| 4,794,533 A | 12/1988 | Cohen | |
| 4,807,642 A | 2/1989 | Brown | |
| 4,817,628 A | 4/1989 | Zealear et al. | |
| 4,950,069 A | 8/1990 | Hutchinson | |
| 4,964,411 A | 10/1990 | Johnson et al. | |
| 5,016,282 A | 5/1991 | Tomono et al. | |
| 5,031,228 A | 7/1991 | Lu | |
| 5,219,322 A | 6/1993 | Weathers | |
| 5,247,938 A | 9/1993 | Silverstein et al. | |
| 5,259,390 A | 11/1993 | Maclean | |
| 5,507,291 A | 4/1996 | Stirbl et al. | |
| 5,572,596 A | 11/1996 | Wildes et al. | |
| 5,619,571 A | 4/1997 | Sandstrom et al. | |
| 5,647,834 A | 7/1997 | Ron | |
| 5,649,061 A | 7/1997 | Smyth | |
| 5,663,900 A | 9/1997 | Bhandari et al. | |
| 5,666,215 A | 9/1997 | Fredlund et al. | |
| 5,725,472 A | 3/1998 | Weathers | |
| 5,741,217 A | 4/1998 | Gero | |
| 5,760,917 A | 6/1998 | Sheridan | |
| 5,762,611 A | 6/1998 | Lewis et al. | |
| 5,772,591 A | 6/1998 | Cram | |
| 5,774,591 A | 6/1998 | Black et al. | |
| 5,802,220 A | 9/1998 | Black et al. | |
| 5,825,355 A | 10/1998 | Palmer et al. | |
| 5,886,683 A | 3/1999 | Tognazzini et al. | |
| 5,898,423 A | 4/1999 | Tognazzini et al. | |
| 5,920,477 A | 7/1999 | Hoffberg et al. | |
| 5,945,988 A | 8/1999 | Williams et al. | |
| 5,959,621 A | 9/1999 | Nawaz et al. | |
| 5,969,755 A | 10/1999 | Courtney | |
| 5,983,129 A | 11/1999 | Cowan et al. | |
| 5,987,415 A | 11/1999 | Breese et al. | |
| 6,004,061 A | 12/1999 | Manico et al. | |
| 6,004,312 A | 12/1999 | Finneran et al. | |
| 6,008,817 A | 12/1999 | Gilmore, Jr. | |
| 6,026,321 A | 2/2000 | Miyata et al. | |
| 6,026,322 A | 2/2000 | Korenman et al. | |
| 6,056,781 A | 5/2000 | Wassick et al. | |
| 6,067,565 A | 5/2000 | Horvitz | |
| 6,088,040 A | 7/2000 | Oda et al. | |
| 6,099,319 A | 8/2000 | Zaltman et al. | |
| 6,134,644 A | 10/2000 | Mayuzumi et al. | |
| 6,182,098 B1 | 1/2001 | Selker | |
| 6,185,534 B1 | 2/2001 | Breese et al. | |
| 6,195,651 B1 | 2/2001 | Handel et al. | |
| 6,212,502 B1 | 4/2001 | Ball et al. | |
| 6,222,607 B1 | 4/2001 | Szajewski et al. | |
| 6,309,342 B1 | 10/2001 | Blazey et al. | |
| 6,327,580 B1 | 12/2001 | Pierce et al. | |
| 6,349,290 B1 | 2/2002 | Horowitz et al. | |
| 6,351,273 B1 | 2/2002 | Lemelson et al. | |
| 6,437,758 B1 | 8/2002 | Nielsen et al. | |
| 6,443,840 B2 | 9/2002 | Von Kohorn | |
| 6,530,082 B1 | 3/2003 | Del Sesto et al. | |
| 6,577,329 B1 | 6/2003 | Flickner et al. | |
| 6,629,104 B1 | 9/2003 | Parulski et al. | |
| 6,792,458 B1 | 9/2004 | Muret et al. | |
| 6,847,376 B2 | 1/2005 | Engeldrum et al. | |
| 7,003,139 B2 | 2/2006 | Endrikhovski et al. | |
| 7,013,478 B1 | 3/2006 | Hendricks et al. | |
| 7,113,916 B1 | 9/2006 | Hill | |
| 7,120,880 B1 | 10/2006 | Dryer et al. | |
| 7,197,459 B1 | 3/2007 | Harinarayan et al. | |
| 7,233,684 B2 | 6/2007 | Fedorovskaya et al. | |
| 7,246,081 B2 | 7/2007 | Hill | |
| 7,263,474 B2 | 8/2007 | Fables et al. | |
| 7,266,582 B2 | 9/2007 | Stelting | |
| 7,307,636 B2 | 12/2007 | Matraszek et al. | |
| 7,319,780 B2 | 1/2008 | Fedorovskaya et al. | |
| 7,327,505 B2 | 2/2008 | Fedorovskaya et al. | |
| 7,350,138 B1 | 3/2008 | Swaminathan et al. | |
| 7,353,399 B2 | 4/2008 | Ooi et al. | |
| 7,355,627 B2 | 4/2008 | Yamazaki et al. | |
| 7,428,318 B1 | 9/2008 | Madsen et al. | |
| 7,474,801 B2 | 1/2009 | Teo et al. | |
| 7,496,622 B2 | 2/2009 | Brown et al. | |
| 7,549,161 B2 | 6/2009 | Poo et al. | |
| 7,551,755 B1 | 6/2009 | Steinberg et al. | |
| 7,555,148 B1 | 6/2009 | Steinberg et al. | |
| 7,558,408 B1 | 7/2009 | Steinberg et al. | |
| 7,564,994 B1 | 7/2009 | Steinberg et al. | |
| 7,573,439 B2 | 8/2009 | Lau et al. | |
| 7,580,512 B2 | 8/2009 | Batni et al. | |
| 7,584,435 B2 | 9/2009 | Bailey et al. | |
| 7,587,068 B1 | 9/2009 | Steinberg et al. | |
| 7,610,289 B2 | 10/2009 | Muret et al. | |
| 7,620,270 B2 | 11/2009 | Matraszek et al. | |
| 7,620,934 B2 | 11/2009 | Falter et al. | |
| 7,644,375 B1 | 1/2010 | Anderson et al. | |
| 7,676,574 B2 | 3/2010 | Glommen et al. | |
| 7,826,657 B2 | 11/2010 | Zhang et al. | |
| 7,830,570 B2 | 11/2010 | Morita et al. | |
| 7,921,036 B1 | 4/2011 | Sharma | |
| 7,933,474 B2 | 4/2011 | Matraszek et al. | |
| 8,010,458 B2 | 8/2011 | Galbreath et al. | |
| 8,159,519 B2 | 4/2012 | Kurtz et al. | |
| 8,184,916 B2 | 5/2012 | Matraszek et al. | |
| 8,401,248 B1 | 3/2013 | Moon | |
| 8,600,120 B2 | 12/2013 | Gonion et al. | |
| 2001/0033286 A1 | 10/2001 | Stokes et al. | |
| 2001/0041021 A1 | 11/2001 | Boyle et al. | |
| 2002/0007249 A1 | 1/2002 | Cranley | |
| 2002/0030665 A1 | 3/2002 | Ano | |
| 2002/0042557 A1 | 4/2002 | Bensen et al. | |
| 2002/0054174 A1 | 5/2002 | Abbott et al. | |
| 2002/0084902 A1 | 7/2002 | Zadrozny et al. | |
| 2002/0171551 A1 | 11/2002 | Eshelman et al. | |
| 2002/0182574 A1 | 12/2002 | Freer | |
| 2003/0035567 A1 | 2/2003 | Chang et al. | |
| 2003/0037041 A1 | 2/2003 | Hertz | |
| 2003/0078513 A1 | 4/2003 | Marshall | |
| 2003/0093784 A1 | 5/2003 | Dimitrova et al. | |
| 2003/0191682 A1 | 10/2003 | Shepard et al. | |
| 2004/0181457 A1 | 9/2004 | Biebesheimer | |
| 2004/0210159 A1 | 10/2004 | Kibar | |
| 2005/0187437 A1 | 8/2005 | Matsugu | |
| 2005/0289582 A1 | 12/2005 | Tavares et al. | |
| 2006/0019224 A1 | 1/2006 | Behar et al. | |
| 2006/0115157 A1 | 6/2006 | Mori | |
| 2006/0200745 A1 | 9/2006 | Furmanski et al. | |
| 2006/0235753 A1 | 10/2006 | Kameyama | |
| 2007/0113181 A1 * | 5/2007 | Blattner et al. | 715/706 |
| 2007/0203426 A1 | 8/2007 | Kover et al. | |
| 2007/0255831 A1 | 11/2007 | Hayashi et al. | |
| 2007/0299964 A1 | 12/2007 | Wong et al. | |
| 2008/0091512 A1 | 4/2008 | Marci et al. | |
| 2008/0101660 A1 | 5/2008 | Seo | |
| 2008/0103784 A1 | 5/2008 | Wong et al. | |
| 2008/0208015 A1 | 8/2008 | Morris et al. | |
| 2008/0214903 A1 | 9/2008 | Orbach | |
| 2008/0222671 A1 | 9/2008 | Lee et al. | |
| 2009/0006206 A1 | 1/2009 | Groe | |
| 2009/0083421 A1 | 3/2009 | Glommen et al. | |

(56) References Cited

U.S. PATENT DOCUMENTS

| | | |
|---|---|---|
| 2009/0094286 A1 | 4/2009 | Lee et al. |
| 2009/0133047 A1 | 5/2009 | Lee et al. |
| 2009/0133048 A1 | 5/2009 | Gibbs et al. |
| 2009/0150919 A1* | 6/2009 | Lee et al. .................. 725/10 |
| 2009/0164132 A1 | 6/2009 | Jung et al. |
| 2009/0195392 A1 | 8/2009 | Zalewski |
| 2009/0270170 A1 | 10/2009 | Patton |
| 2009/0271417 A1 | 10/2009 | Toebes et al. |
| 2009/0299840 A1 | 12/2009 | Smith |
| 2009/0300525 A1* | 12/2009 | Jolliff et al. .................. 715/764 |
| 2010/0070523 A1 | 3/2010 | Delgo et al. |
| 2010/0099955 A1 | 4/2010 | Thomas et al. |
| 2010/0198757 A1 | 8/2010 | Cheng et al. |
| 2010/0240416 A1 | 9/2010 | Knight |
| 2010/0266213 A1 | 10/2010 | Hill |
| 2010/0274847 A1 | 10/2010 | Anderson et al. |
| 2011/0092780 A1 | 4/2011 | Zhang et al. |
| 2011/0126226 A1 | 5/2011 | Makhlouf |
| 2011/0143728 A1 | 6/2011 | Holopainen et al. |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0293548 A1 | 11/2012 | Perez et al. |
| 2012/0304206 A1 | 11/2012 | Roberts et al. |

FOREIGN PATENT DOCUMENTS

| | | | |
|---|---|---|---|
| KR | 10-2008-0016303 A | | 2/2008 |
| KR | 1020100048688 A | | 5/2010 |
| KR | 100964325 B1 | | 6/2010 |
| KR | 1020100094897 A | | 8/2010 |
| WO | WO 2011/045422 A1 | | 4/2011 |

OTHER PUBLICATIONS

International Search Report dated Nov. 14, 2011 for PCT/US2011/039282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

* cited by examiner

USING AFFECT WITHIN A GAMING CONTEXT

RELATED APPLICATIONS

This application claims the benefit of U.S. provisional patent applications "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, "Baseline Face Analysis" Ser. No. 61/467,209, filed Mar. 24, 2011, "Mental State Analysis of Voters" Ser. No. 61/549,560, filed Oct. 20, 2011, "Mental State Evaluation Learning for Advertizing" Ser. No. 61/568,130, filed Dec. 7, 2011, "Affect Based Concept Testing" Ser. No. 61/580,880, filed Dec. 28, 2011, and "Affect Based Evaluation of Advertisement Effectiveness" Ser. No. 61/581,913, filed Dec. 30, 2011. This application is also a continuation-in-part of U.S. patent application "Mental State Analysis Using Web Services" Ser. No. 13/153,745, filed Jun. 6, 2011 which claims the benefit of U.S. provisional patent application "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. This application is also a continuation-in-part of U.S. patent application "Sharing Affect Across a Social Network" Ser. No. 13/297,342, filed Nov. 16, 2011 which claims the benefit of U.S. provisional patent application "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, "Baseline Face Analysis" Ser. No. 61/467,209, filed Mar. 24, 2011, and "Mental State Analysis of Voters" Ser. No. 61/549,560, filed Oct. 20, 2011. Each of the foregoing applications is hereby incorporated by reference in its entirety.

FIELD OF INVENTION

This application relates generally to analysis of mental states and more particularly to using affect within a gaming context.

BACKGROUND

Computer gaming is an enormously popular activity that is enjoyed by a large portion of the population. Children, teenagers, and even adults have all enjoyed video gaming as a pastime, for educational purposes, for training, for exercise, and the like. Computer games may include a wide range of genres such as sporting events and activities, automotive driving and racing, aircraft and spacecraft flight, fantasy themes, updated board games, social games and activities, military-oriented and "first person shooter" games, etc. Various age groups have enjoyed creative and engaging computer gaming activities.

Many computer games incorporate a competitive, multi-player component into their design. This aspect of the games heightens competition and has led to shared enjoyment of a game by two or more players. While at first the two or more players may have been collocated with a computer game, it is now common that the multiplicity of players is dispersed across a large geographical area. In some cases, the players may be dispersed across multiple time zones around the globe. Nonetheless, because of the immersive nature of the video games, there is a real and vibrant sense of community that can develop among the gamers. Individuals in the community can work on game strategy, contribute to game enhancements, and even develop interpersonal friendships that transcend the gaming experience. The gaming environment has become a way for people and teams of people to have interpersonal interactions with likeminded players. Gamers want to share various aspects of their gaming experiences with each other in order to feel that they are an integral part of the game. As a result, game players can spend a tremendous amount of time involved with these games.

Computer gaming enthusiasts concur that the more immersive the computer game, the greater the degree of satisfaction that can be derived from it. Thus, computer game developers strive to create an immersive experience (in some cases intensely so). Sight, sound, physical gestures, and now various creative controlling schemes all contribute to the sense that the gamer has become an integral part of the game. Thus, the more interactive the interface, the greater and more enjoyable the gaming experience.

Many types of computer interfaces and enhancements exist which can be used to interact with and control a computer game. For example, a screen or multiple screens used by the ubiquitous graphical user interfaces (GUI) may be substituted with a touch screen, thus allowing the user to manipulate the game by touch. This latter adaptation is common with handheld devices. Interfaces allow manipulation of simulated objects and their properties. Tangible user interfaces enable touch and physical feedback (i.e. force feedback) for working in physical environments or their elements. Task-focused interfaces are enhancements that address the "information overload" problem by allowing the user to focus on tasks rather than a multitude of specific elements. Zooming interfaces allow for changes in levels of detail about objects, thus permitting zooming in on specific aspects from sets of elements.

Another interface class uses sensors to collect inputs. For example, an interface may include user voice activation that permits information capture, control, etc. Further, motion recognition is becoming a popular gaming interface. Such activity-interface devices may include a gamepad, paddle, trackball, joystick, a throttle, steering wheels, aircraft type yokes (oriented to aircraft control), pedals (vehicle control), keyboard and mouse, touch screen, motion sensing, and a light gun. Other gesture recognition devices are purpose-oriented, such as pinball controllers, dance pads, balance boards, rhythm game devices (keyboards, guitars, drums, microphones, etc.), buzzers (like those used in game shows), sports equipment (fishing rods, tennis racquets), and the like.

SUMMARY

Analysis of people as they interact with a gaming environment may be performed by gathering mental states through evaluation of facial expressions, head gestures, and physiological conditions. This analysis may be used to inform others in a social network of the mental states of people interacting with the game. The analysis may also be used to modify the gaming experience. A computer implemented method for gaming is disclosed comprising: collecting mental state data of an individual while the individual is involved in a game; analyzing, using a web services server, the mental state data to produce mental state information; and modifying the game based on the mental state information. The collecting mental state data may further comprise collecting one or more of facial data, physiological data, and actigraphy data. A webcam may be used to capture one or more of the facial data and the physiological data. The method may further comprise inferring mental states with regard to the game based on the mental state data which was collected wherein the mental states include one or more of frustration, confusion, disappointment, hesitation, cognitive overload, focusing, engagement, attention, boredom, exploration, confidence, trust, delight, disgust, skepticism, doubt, satisfaction, excitement, laughter, calmness, stress, and curiosity. The game may be within an electronic gaming environment. The modifying the game may include modifying an avatar that represents the individual. The avatar may be animated based on the mental state information.

The modifying the game may include changing tasks with which the individual is presented. The changing tasks may include making the game harder. The mental state information may include an indication of boredom. The changing tasks may include making the game easier. The mental state information may include an indication of frustration. The game may be a multiplayer game. The modifying the game may include modifying an avatar that represents a group of people who are playing the multiplayer game. The avatar may represent a collective mental state for the group of people. The multiplayer game may include requiring players to imitate a face. The multiplayer game may include an objective of achieving a collective mental state. The multiplayer game may include an objective of avoiding a collective mental state. The game may include an objective of achieving a mental state by the individual. The game may include an objective of avoiding a mental state by the individual. The method may further comprise developing a mental state for a computer generated player. The computer generated player may compete against the individual. The computer generated player may be on a team with the individual.

In embodiments, a computer implemented method for gaming may comprise: collecting mental state data of an individual while the individual is involved in a gaming environment; analyzing the mental state data to produce mental state information; and sharing the mental state information across a social network. In some embodiments, a computer implemented method for gaming may comprise: collecting mental state data of an individual while the individual is involved in a game within a gaming environment; analyzing, using a web services server, the mental state data to produce mental state information; and displaying the mental state information in a visualization.

In embodiments, a computer program product stored on a non-transitory computer-readable medium for gaming may comprise: code for collecting mental state data of an individual while the individual is involved in a game; code for analyzing, using a web services server, the mental state data to produce mental state information; and code for modifying the game based on the mental state information. In some embodiments, a computer system for gaming may comprise: a memory for storing instructions; one or more processors attached to the memory wherein the one or more processors are configured to: collect mental state data of an individual while the individual is involved in a game; analyze, using a web services server, the mental state data to produce mental state information; and modify the game based on the mental state information.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

The present disclosure provides a description of various methods and systems for analyzing people's mental states as they interact with a gaming environment. Use of emotions in the midst of gaming can provide enormous possibilities. Historically, board games were played around a dining room or coffee table. With the advent of electronic gaming, participants were now at significant distance from one another. Due to this distance the gamers could not obviously perceive how opponents were feeling. With the disclosed concept, gamers can now understand the emotions their opponents or teammates are experiencing. Affect can be communicated across a distance. Beyond that, the electronic game itself can perceive a person's mental states and adapt the game accordingly.

A mental state may be an emotional state or a cognitive state. Examples of emotional states include happiness or sadness. Examples of cognitive states include concentration or confusion. Observing, capturing, and analyzing these mental states can yield significant information about people's reactions to a game that far exceed previous capabilities in gaming. Analysis of the mental states may be provided by web services where modifications to the games can be provided. Some terms commonly used in evaluation of mental states are arousal and valence. Arousal is an indication on the amount of activation or excitement of a person. Valence is an indication on whether a person is positively or negatively disposed. Affect may include analysis of arousal and valence. Affect may also include facial analysis for expressions such as smiles or brow furrowing.

Figure 1:
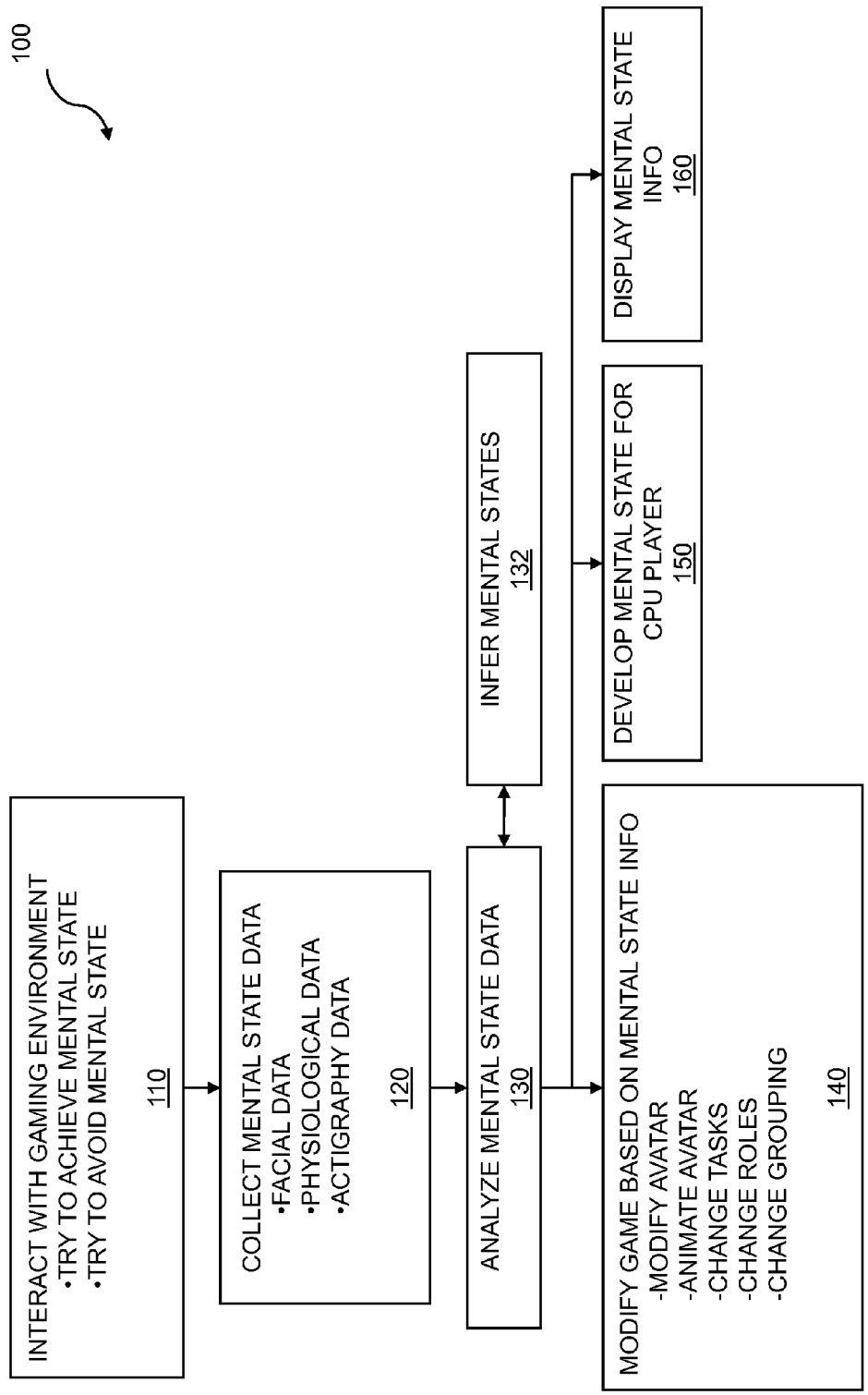
FIG. 1 is a flow diagram representing gaming interaction.

FIG. 1 is a flow diagram representing gaming interaction. A flow 100 is shown for a computer implemented method for gaming. The flow 100 may begin with an individual or group of people interacting with a gaming environment 110. In the gaming environment, an individual may play a game which is a computer game, a video game, a personal game, a kinetic game, or the like. The game could be for entertainment, for education, for training, for simulating an experience, and so on. In some cases, the game could be for helping in training for a profession such as being a pilot, astronaut, doctor, surgeon, psychologist, manager, teacher, and so on. In some cases, the game may be part of a therapeutic exercise to help in mental health wellness.

The game may be a typical game or a game especially developed to take advantage of mental state capabilities. In some embodiments, the game may include requiring one or more players to imitate a face. Based on facial expression analysis a match or a close match to the face to imitate may be obtained. The face to be imitated may be a reflection of a certain mental state such as happy, sad, or the like. In some cases the face to be imitated may be of an expression to intimidate, persuade, be compassionate, be aloof, etc. The game may include an objective of achieving a mental state by the individual. This type of game may be used as part of a therapeutic effort where the person is to try to reach a state of contentedness or happiness as opposed to being depressed. In some embodiments, the game may include an objective of avoiding a mental state by the individual. In some cases a multiplayer game may include an objective of achieving a collective mental state by a group of people. Alternatively, the objective may be for the individual to get another person or a group of people to achieve the mental state. In some cases, the objective may be for a group to achieve the mental state. In some embodiments, the game may include an objective of avoiding a collective mental state. For example, the game may be a group of comedy presentations and the objective is to avoid smiling or laughing. There may be a contest between multiple teams to see which team can be the most stoic.

The flow 100 continues with collecting mental state data 120 of an individual while the individual is involved in a game. The collecting of mental state data may further comprise collecting one or more of facial data, physiological data, and actigraphy data. The mental state data may be collected by a gaming machine which is part of the gaming environment. Alternatively, the mental state data may be collected by a peripheral device or computer which has access to the individual. In some embodiments, a webcam may be used to capture one or more of the facial data and the physiological data. In embodiments, the physiological data and actigraphy data may be obtained from one or more biosensors attached to an individual.

The flow 100 continues with analyzing, using a web services server, the mental state data 130 to produce mental state information. The web services server may be a remote computer from the game machine. The server may provide game information to the gaming machine and may facilitate play between multiple players. The analyzing can include aggregating mental state information with others who are playing or have played the game. While mental state data may be raw data, mental state information may include the raw data or information derived from the raw data. The mental state information may include all of the mental state data or a subset thereof. The mental state information may include valence and arousal. The mental state information may include information on the mental states experienced by a gamer. Some analysis may be performed on a client computer before that data is uploaded while some analysis may be performed on a server computer. Analysis of the mental state data may take many forms and may be based on one person or a plurality of people. In some embodiments, the mental state information is propagated to a social network. Through the social network others may be made aware of the affect of the individual as they interact with the gaming environment. In some embodiments, the analysis may help an individual identify when they smirk, are condescending, trivializing another's experience, or exhibit some other behavior that is desired to be modified or corrected. In some cases, the game may be poker or another game of chance. The mental state analysis may allow a computer or other player to predict the type poker hand an individual has.

The flow 100 may include inferring mental states 132 with regard to the game based on the mental state data which was collected. The inferred mental states may include one or more of frustration, confusion, disappointment, hesitation, cognitive overload, focusing, engagement, attention, boredom, exploration, confidence, trust, delight, disgust, skepticism, doubt, satisfaction, excitement, laughter, calmness, stress, and curiosity. The inferring of mental states may be done for an individual or for a plurality of people who are playing the game.

The flow 100 continues with modifying the game based on the mental state information 140. The game may be modified in numerous ways which those of skill in the art will be familiar. The modifying the game may include modifying an avatar that represents the individual. The avatar may be selected by the individual. Alternatively, the avatar may be selected by the game based, at least in part, on the mental states of the individual. The avatar may be animated based on the mental state information. For example, if the individual is excited, the avatar may move around the game in an excited fashion. In some embodiments, the modifying the game may include modifying an avatar that represents a group of people who are playing the multiplayer game. The avatar may represent a collective mental state for the group of people.

The modifying the game may include changing tasks with which the individual is presented. Many games include a sequence of challenges which must be overcome as the player progresses through the game. The type of challenge or task may be modified based on the mental states of the individual. The changing tasks may include making the game harder. The making the game harder may be based on the mental state information including an indication of boredom. In some embodiments, changing tasks may include making the game easier. The making the game easier may be based on the mental state information including an indication of frustration.

The game may be a multiplayer game. The multiple people in the game may be together in one room, as in a party game. Alternatively, the multiple people may be connected through a network such as the Internet. The modifying the game may include changing tasks presented in the multiplayer game. The sequence of challenges may be modified in order or in character. In the case of a dance game, the types of dance and music may be modified. The modifying may include changing roles within a team. With multiple players, differing roles may be needed for the multiple players which make up the team. In one example, a person who is more confident may be selected to be a team leader. In another example, a person who is calmer may be chosen to be the collector of the supplies. The modifying may include grouping the individual with others based on the mental state of the individual. When a multiplayer team has two or more teams which play against each other, such as in a sporting or military type game, the grouping of sides may be modified. For example, a mix of confident and nervous people may be combined on each team so that both experienced and new people are shared between teams. The modifying the game may include changing a role for the individual. For example, when a person starts to exhibit mental states associated with tedium, their role may be changed within the game. The modifying the game may include advancing the individual through game levels. For example, when a person exhibits unusual confidence they may be allowed to skip levels within a game to move them to more challenging game scenarios.

In some games, an individual plays against or with a computer generated player. The flow 100 may include developing a mental state for a CPU or computer generated player 150. The computer generated player may compete against the individual. The computer generated player may be on a team with the individual. The computer generated player could respond to the individual's affect. For example the computer generated player may inject a more engaging persona to enliven the game when a person starts to slow down or take on an affect that reflects being tired, bored, or disinterested.

The game may be a party game. The party game may be modified to develop a community mental state where the mental state of the individual is aggregated within the community mental state. For example, a special event may be offered if a certain number of people achieve a certain state of excitement. For instance, if a group of gamers all smile at the same time then a new game level may be released for the next 24 hours free of charge.

In some embodiments, flow 100 includes displaying the mental state information 160 in a visualization. The visualization may be graphical or textual presentation of the mental state information. The visualization may be used within a social network to easily grasp how the individual is reacting to the gaming environment. Alternatively, the visualization may be used by game developers or market researchers to better understand the individual's reaction to the game or a portion thereof. Optimal product placement and advertisements could be included based on the visualization. Various steps in the flow 100 may be changed in order, repeated, omitted, or the like without departing from the disclosed inventive concepts. Various embodiments of the flow 100 may include a computer program product embodied in a non-transitory computer readable medium that includes code executable by one or more processors.

Figure 2:
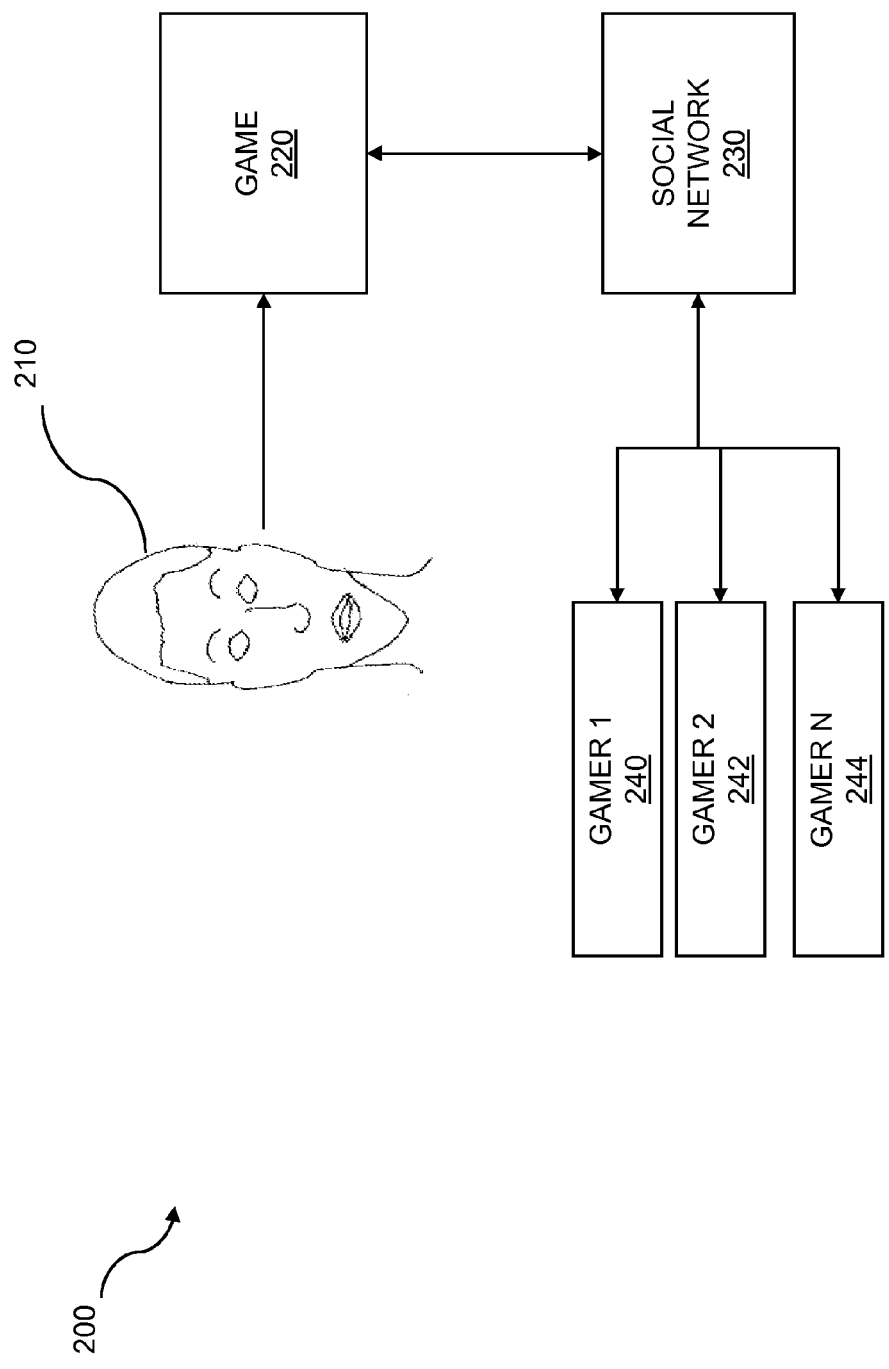
FIG. 2 is a diagram showing social network/gaming interaction.

FIG. 2 is a diagram showing social network/gaming interaction. A person 210 is shown interacting with a game 220. The game 220 may be a computer game, a video game, a personal game, a kinetic game, or the like. A kinetic game can be considered a motion oriented game such as the Nintendo Wii™, Microsoft Kinect™, Sony PlayStation Move™. The person 210 may interact with the game using a keyboard, a mouse, a joystick, a game controller, a game remote, a motion sensor, a camera sensor, or some other device. As the person 210 interacts with the game 220, the mental states of the person 210 may be observed and/or analyzed. The mental states of the person may be captured based on a webcam, a video camera, or other camera device. Facial data obtained from a webcam may include facial actions and head gestures which may in turn be used to infer mental states. The mental states may also be captured using a biosensor. The biosensor may capture information on electrodermal activity (EDA) or skin conductance or galvanic skin response (GSR), accelerometer readings, skin temperature, heart rate, heart rate variability, and other types of physiological analysis of an individual. The video and physiological observations may be performed and analyzed locally. Alternatively, the video and physiological observations may be captured locally on a client machine with analysis being performed on a remote server machine.

Information on the game 220 along with mental state information on the person 210 is communicated to a gaming server or to a social network 230. The social network 230 may be Facebook™, Myspace™, Steam™, Twitter™, or other social structure. The social structure may be made up of nodes, where each node represents an individual or organization, and where various nodes have an interdependency and communication is possible between various nodes. The social network 230 may comprise a gaming community. Affect, based on camera or on physiological observations, is communicated to the social network 230. Other individuals who are part of the social network 230 may participate in the game 220. For example, gamer 1 240, gamer 2 242, through gamer N 244 may be part of the game 220 that the person 210 is playing. In some embodiments, the gamers may be considered to be a clan. The mental states of the person 210 may be presented to the other gamers. Likewise, the mental states of the other gamers may be presented to the person 210. The mental state of the person 210 may be presented to the other gamers who are part of the social network 230 through an avatar representation, through a set of color representations, or through a graphical representation. Likewise the mental state information may be represented in one of a group selected from a bar graph, a line graph, a smiling face, a frowning face, and a text format or the like. In some embodiments, affect is communicated to the social network 230.

Communication of affect can be real time while the game 220 is being played. In some embodiments, the game 220 can be modified based on this real time affect communication. Alternatively, communication of affect can be after the game 220 is completed or after a specific session or goal of the game 220 is completed. The affect can be communicated as a single graphical representation such as a graph, an avatar, or a smiley face. The graphical representation could be a set of stars, hearts, or other symbol that can connotate positive or negative rating. The affect can be communicated numerically, with the number indicating a positive or negative experience with the game 220 or a portion of the game. A set of thumbnails can be displayed where the thumbnails are snapshots of the game 220 as it is played. Another set of thumbnails can be displayed of facial expressions from the person 210 as he or she interacts with the game 220.

In some embodiments, affect can be communicated to the social network 230 where some or all of the people are not gamers playing the game 220. The people on the social network 230 may want to know what activities the person 210 is involved with, including such activities as the game 220, and the reaction of the person 210 to the activities. The reaction can include the affect of the person 210. The person's reaction to the game 210 can be used to recommend the game 210 or a part of the game to others on the social network 230.

It will be understood that throughout this disclosure, that while a reference may be made to an individual or a person with respect to the gaming, mental state collection, analysis, sharing, and the like that the concepts apply equally to groups of people playing games. The people may be in the same room or may be remote from one another playing across a network such as the Internet. All such embodiments for both groups and individuals fall within the scope of this disclosure.

Figure 3:
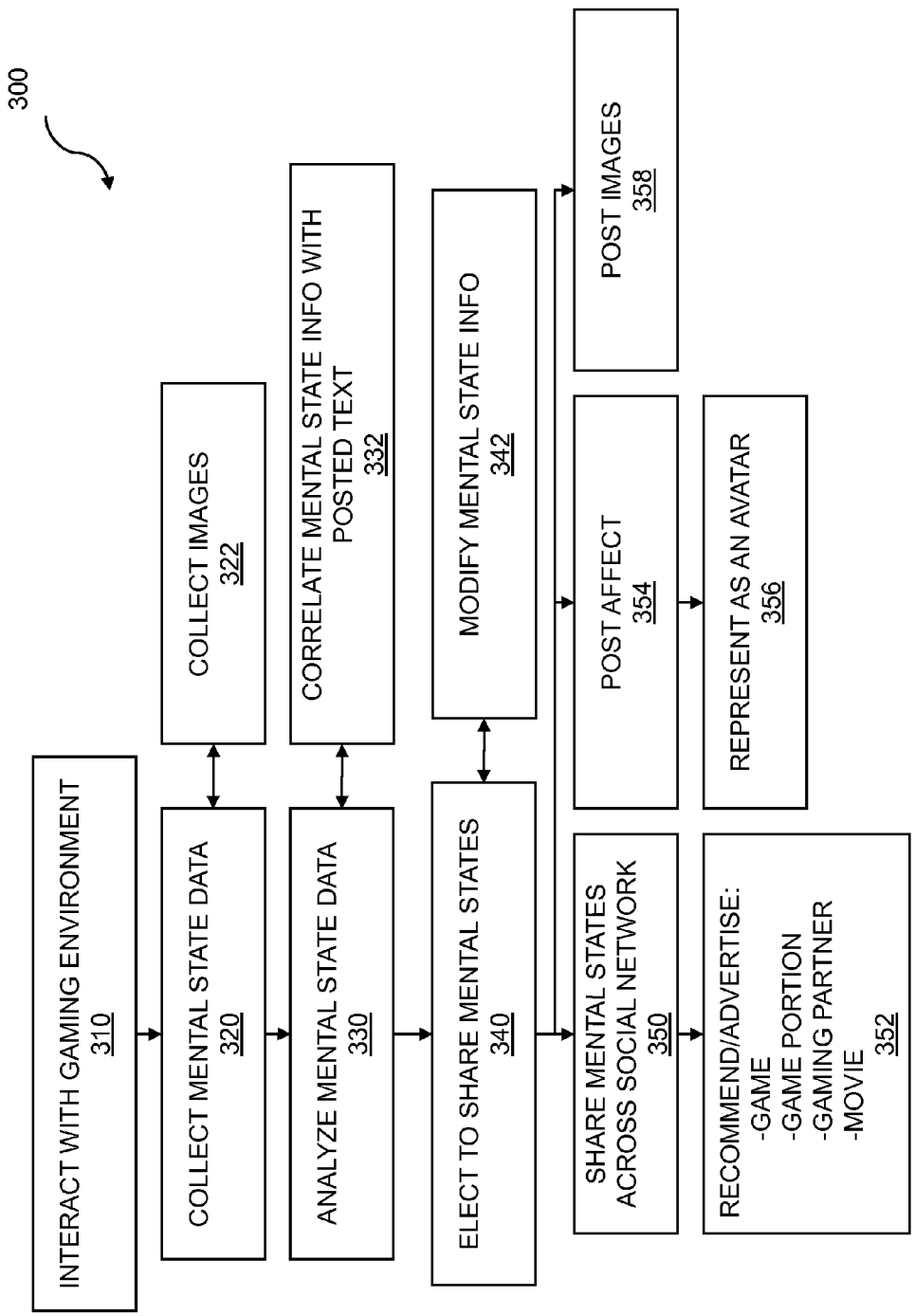
FIG. 3 is a flow diagram showing social network interaction with gaming.

FIG. 3 is a flow diagram showing social network interaction with gaming. A flow 300 describes a computer implemented method for gaming. The flow 300 begins with an individual interacting with a gaming environment 310. The gaming environment may include a computer game, a video game, a personal game, a kinetic game, or the like. The flow 300 continues with collecting mental state data 320 of the individual while the individual is involved in the gaming environment. The mental state data may be based on facial expressions and physiological data. The mental state data may include collecting action units. Alternatively mental state data may involve collecting facial expressions, such as smiles or brow furrows. Physiological data may be obtained from video observations of a person. For example, heart rate, heart rate variability, autonomic activity, respiration, and perspiration may be observed from video capture. Alternatively, in some embodiments, a biosensor may be used to capture physiological information and may also be used to capture accelerometer readings. The flow 300 continues with analyzing the mental state data 330 to produce mental state information. In some embodiments, mental state data collection and mental state analysis may be performed in a single step. Additionally, in some embodiments, the analyzing of the mental state information may be analyzed along with posted text to correlate the mental state information with the posted text 332. Posted text could take the form of text input for a game, blog entries, Twitter™ comments, and the like. When the mental state data is analyzed, the game may be modified based on the individual's affect. For instance, music played along with the game could be modified based on the heart rate of the individual. The music tempo and volume could each be increased if a person starts to become disinterested. In another example, the pace of the game could be modulated based on the engagement or activation of the gamer. Likewise a scene within the game could be modified to help calm a person that is becoming agitated.

The analyzing of mental state data may include inferring of mental states for the individual as they interact with the gaming environment 310. The analyzing may be performed locally on a client computer system. The analyzing may be performed on a server computer or other remote system.

The flow 300 continues with sharing the mental state information across a social network 350. The social network may comprise a gaming community. People on the social network who receive the mental state information may themselves be gamers. In some cases, however, the people on the social network who receive the mental state information may only be participants in the social network and not gamers themselves or at least not involved with the game with which the individual is interacting. Those people may only be interested in the individual and any activities or reactions of the individual. The sharing of mental states could replace or augment other rating systems. For example, other rating systems include selecting whether the individual liked, disliked, loved, etc. a game or video. The affect for the person could be used to augment such a rating system. Alternatively the person's affect could replace and be used as the only rating system for games, videos, and the like. In some embodiments, an affect could be shared across a network which indicates the level of engagement or excitement for the individual. For example, in a music game the people on the social network could see how excited the individual or the band made up of individuals become when they play certain music or musical instruments. In some embodiments, mental state information may be shared across a social network based on the mental states. For example, with smiles or laughter, by an individual or group of people, mental state information may be propagated across a social network. In embodiments, based on smiles and laughter, mental state information may be propagated by text messaging or Twitter™ to those in a select group. Based on this information others may choose to join in the gaming environment.

In some embodiments, the flow 300 may include a step, before the sharing of mental states, of electing, by the individual, to share the mental state information 340. There may be a stage where the individual can opt in to sharing of mental states in general, only for a specific game, or only for a specific session. In embodiments, the individual may elect to share the mental state information after a session is completed. In other embodiments, the sharing may be real time so that the gaming experience and reactions may be modified real time as the individual is participating in the game. In some embodiments, when a person elects to share mental states the mental state information may be modified 342. For example, a person may chose to share a mental state which is more confident, happier, or positive at certain times than the inferred mental states which were analyzed. In some cases, the flow 300 may include handicapping the affect or mental state. This handicapping may level a playing field for a game where there are more experienced and less experienced players in the same game.

In some embodiments, the flow 300 includes posting affect 354 from the individual to others who are involved in the gaming environment. The posting of affect may be represented through a set of color representations, through a graphical representation, through a set of thumbnails, or through a text communication. The posting of affect may include representation by an avatar 356. The avatar may be static, such as simply showing a smile. The avatar may be animated showing excitement or even activity related to the game in which the individual is participating.

In some embodiments, the flow 300 includes collecting images 322 of the individual while the individual is involved in the gaming environment. These images may be video or may be individual still photographic images. The images may be standard visual light photographs or may include infrared or ultraviolet images. In some embodiments, the flow 300 includes posting an image 358 from a session within the gaming environment. The image may include a facial expression. A group of images may be included as a set of thumbnails. A facial expression may be selected because it is an animated expression. A facial expression may be selected because it is an unusual facial expression. A facial expression may be selected because it is a typical facial expression. In some embodiments, the image posted may include a video of the whole person or face. The images posted can share the highlights of the game being played.

Based on the mental states of the individual, recommendations 352 to or from the individual may be provided. The flow 300 may include recommending a game, based on the mental state information, to others in the social network. A recommendation may include recommending part of a game, based on the mental state information, to others in the social network.

A recommendation may include recommending a gaming partner based on the mental state information. A gaming partner may be recommended based on skill, role, compatibility, or coaching ability. A correlation between an individual and other individuals within the social network to identify those types of gaming partners most preferred. Based on the correlation and the mental states of the individual, a gaming partner may be recommended.

One or more recommendations may be made to the individual based on the mental states of the individual. A game or portion of a game may be recommended to the individual based on his or her mental states as they interact with the game. A correlation may be made between the individual and others with similar affect exhibited during the game. The correlation may include a record of other games or other experiences along with their affect. Likewise a movie, video, video clip, webisode or other activity may be made to individual based on their affect.

The flow 300 may include advertising a game based on the mental state information. An advertisement may be made to the individual because the individual had positive mental states for a certain game and another game would be expected to evoke similar positive mental states. An advertisement may be made to the individual because the individual had negative mental states for a certain game and a different game could be expected to evoke a more positive group of mental states.

Based on mental state correlations with other people in the gaming environment an advertisement could be tailored for the individual.

The flow 300 may include recommending a movie, video, video clip, game, or portion of a game based on the mental state information from the gaming environment. When an individual has a positive set of mental states with a specific gaming experience, a similar movie, television show, web series, webisode, video clip, book, magazine, or other media may be recommended. Various steps in the flow 300 may be changed in order, repeated, omitted, or the like without departing from the disclosed inventive concepts. Various embodiments of the flow 300 may include a computer program product embodied in a non-transitory computer readable medium that includes code executable by one or more processors.

Figure 4:
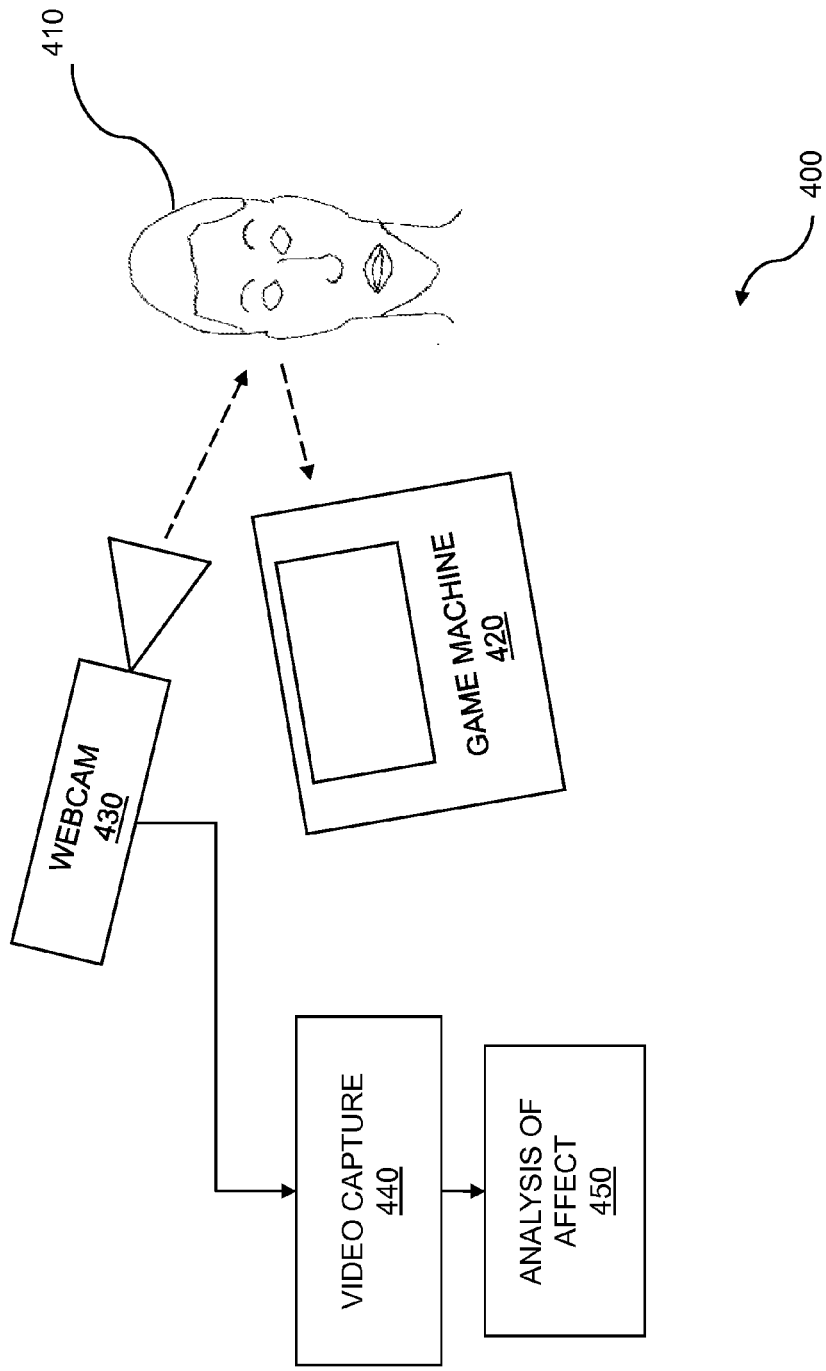
FIG. 4 is a diagram showing image capture during gaming.

FIG. 4 is a diagram showing image capture during gaming. A system 400 includes a game machine 420 and a webcam 430. The system 400 captures facial response to a rendering on the game machine 420 and the experience with the game wherein the game may be within an electronic gaming environment. The facial data may include video and collection of information relating to mental states. In some embodiments, a webcam 430 may capture video of the person 410. A webcam, as the term is used herein and in the claims, may be a video camera, still camera, thermal imager, CCD device, phone camera, three-dimensional camera, a depth camera, multiple webcams used to show different views of a person or any other type of image capture apparatus that may allow data captured to be used in an electronic system.

The game machine 420 will show a rendering relating to gaming action. The game machine may include any electronic display, including but not limited to, a computer display, a laptop screen, a net-book screen, a tablet computer screen, a cell phone display, a mobile device display, a remote with a display, a television, a projector, or the like. The game machine may also include a keyboard, mouse, joystick, touchpad, wand, motion sensor, and other input means. The game may be from a webpage, a website, a web-enabled application, a virtual world, or the like. The images of the person 410 may be captured by a video capture unit 440. In some embodiments, video is captured while in others a series of still images are captured. In embodiments, a webcam is used to capture the facial data.

Analysis of action units, gestures, and mental states may be accomplished using the captured images of the person 410. The action units may be used to identify smiles, frowns, and other facial indicators of mental states. The gestures, including head gestures, may indicate interest or curiosity. For example, a head gesture of moving toward the gaming machine 420 may indicate increased interest or a desire for clarification. Based on the captured images, analysis of physiology may be performed. Analysis of affect 450 may be performed based on the information and images which are captured. The analysis can include facial analysis and analysis of head gestures. The analysis can include analysis of physiology including heart rate, heart variability, respiration, perspiration, temperature, and other bodily evaluation.

Figure 5:
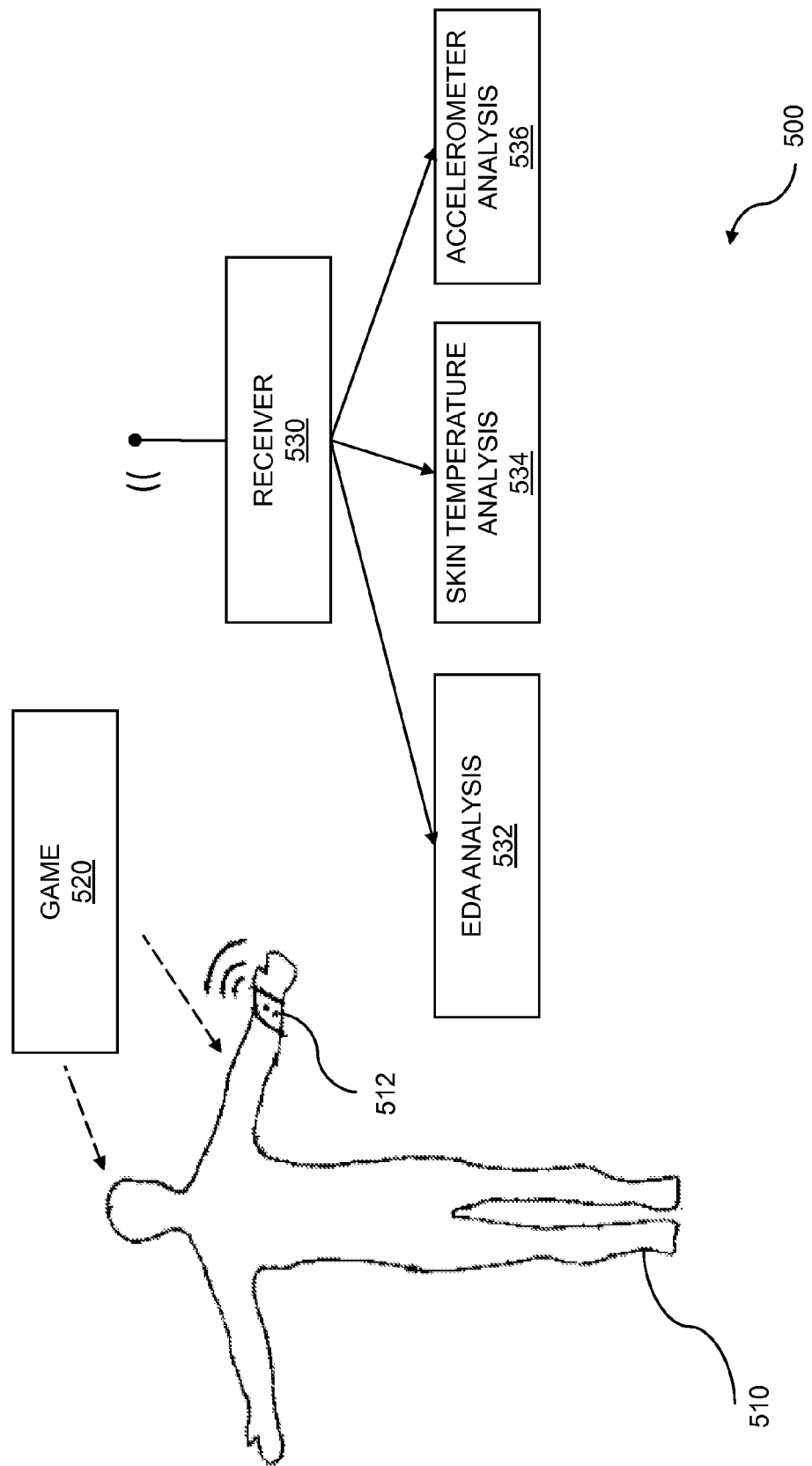
FIG. 5 is a diagram showing sensing and interaction with gaming.

FIG. 5 is a diagram showing sensing and interaction with gaming. A system 500 may analyze a person 510, for whom data is being collected, as the person 510 interacts with a game 520. The game 520 may be a video game, a computer game, a group party game, an educational game, a kinetic game, or other game. The person 510 has a sensor 512 attached to him or her. The sensor 512 may be placed on the wrist, palm, hand, head, or other part of the body. The sensor 512 may include detectors for electrodermal activity, skin temperature, and accelerometer readings. Other detectors may be included as well, such as heart rate, blood pressure, EKG, EEG, further brain waves, and other physiological detectors. The sensor 512 may transmit information collected to a receiver 530 using wireless technology such as Wi-Fi, Bluetooth, 802.11, cellular, or other bands. The receiver may provide the data to one or more components in the system 500. In some embodiments, the sensor 512 will record various physiological information in memory for later download and analysis. In some embodiments, the download of data can be accomplished through a USB port.

Electrodermal activity may be collected in some embodiments and may be collected continuously, every second, four times per second, eight times per second, 32 times per second, or on some other periodic basis as the person 510 interacts with the game 520. In some embodiments, aperiodic sampling may be performed using a Boltzmann distribution or in a lumpy fashion based on events of interest. The electrodermal activity may be recorded. The recording may be to a disk, a tape, onto flash memory, into a computer system, or streamed to a server. The electrodermal activity may be analyzed 532 to indicate arousal, excitement, boredom, or other mental states based on changes in skin conductance. Skin temperature may be collected on a periodic basis or an as needed basis and then be recorded. The skin temperature may be analyzed 534 and may indicate arousal, excitement, boredom, or other mental states based on changes in skin temperature.

Accelerometer data may be collected and indicate one, two, or three dimensions of motion. The accelerometer data may be recorded. The accelerometer data may be analyzed 536 and may indicate gaming activities, motions, and involvement based on accelerometer data.

In some embodiments, multiple sensors 512 may be attached to an individual. In embodiments, the sensors could be incorporated in sweat bands that a person wears. For instance, a sensor could be attached to each wrist and each ankle to detect motions and relative positions of the arms and legs. A sensor could also be attached to the head or elsewhere on the body. In embodiments, the sensor could be used to evaluate motions for certain sporting types of games, such as for example soccer, bowling, or boxing. In embodiments, the sensors could be used to evaluate positions in yoga and have the game help the gamer to learn better body position. Further, sensors could be used to evaluate both motion and emotion. For instance, a golf swing could be evaluated along with whether the gamer was calm during the swing.

Figure 6:
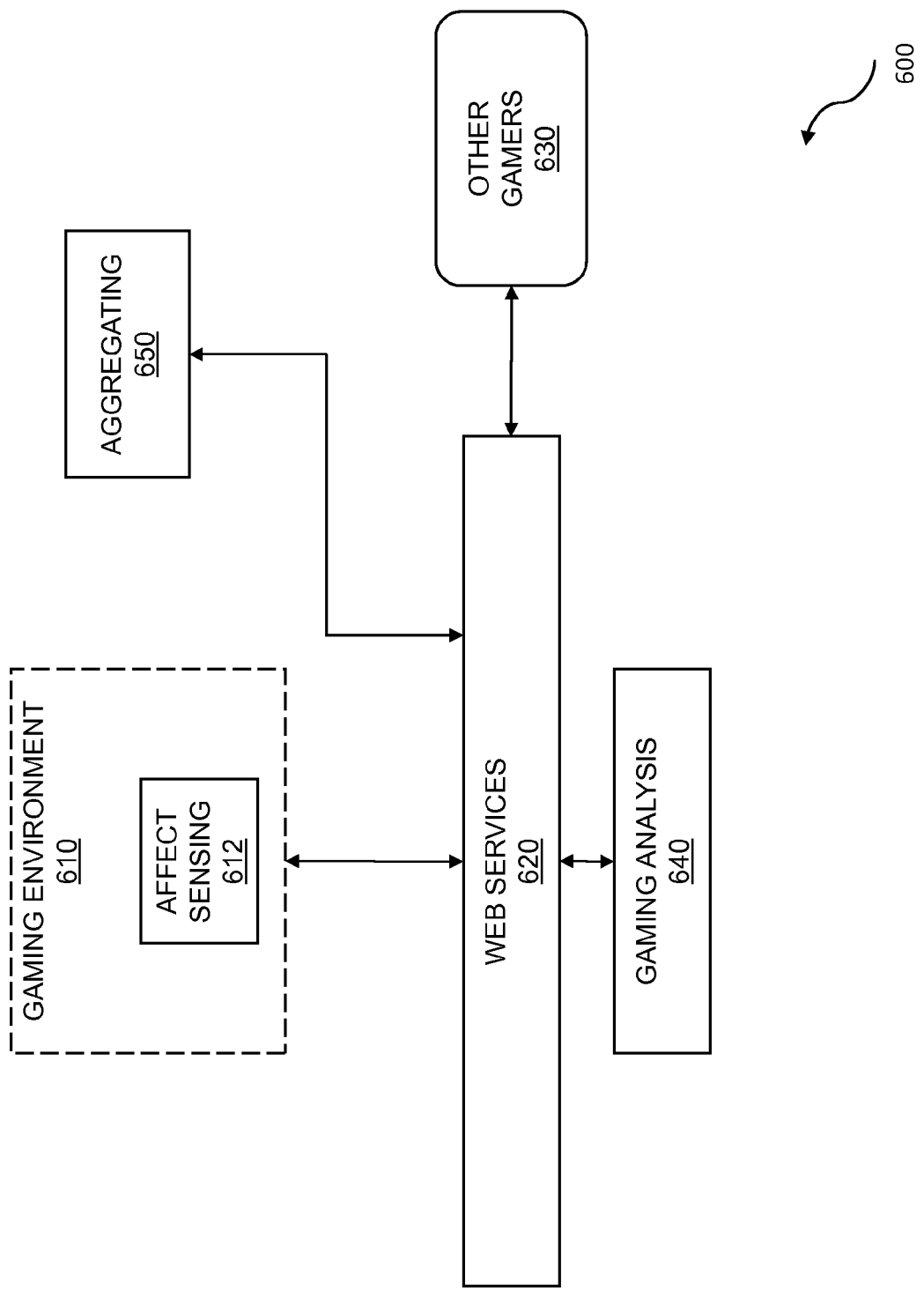
FIG. 6 is a diagram showing web services gaming analysis.

FIG. 6 is a diagram showing web services gaming analysis. The system 600 includes a gaming environment 610 and web services 620. The gaming environment may be supported by a computer game, a video game, a personal game, a kinetic game, or the like. The gaming environment 610 may include affect sensing 612 apparatus for a gamer. The affect sensing 612 may include collecting one or more of facial, physiological, and accelerometer data. The physiological data analysis may include electrodermal activity or skin conductance, skin temperature, heart rate, heart rate variability, respiration, and other types of analysis of a human being. The gaming environment 610 may include the needed hardware for performing the affect sensing. In other embodiments there may be a separate device, such as a laptop, personal computer, or mobile device which captures data associated with the affect sensing 612. The output of the affect sensing 612 can be forwarded for analysis to the web services 620. The web services 620 can be part of a gaming system. Alternatively, the web services 620 can be a separate analysis system which provides input to the gaming system. The web services 620 may be a server or may be a distributed network of computers.

In some embodiments, some analysis may be performed by the affect sensing 612 apparatus. In other embodiments, the affect sensing 612 apparatus collects data and the analysis is performed by the web services 620. Other gamers 630 will be playing the game along with the gamer who is having his or her affect sensed. In embodiments, each of the gamer and the other gamers 630 will have their affect sensed and provided to the web services 620.

Analysis of the affect in the gaming environment is performed by the gaming analysis 640 module. The gaming analysis 640 module may be part of the gaming system, part of the web services 620, or part of a computer system that provides an analysis engine. The facial, physiological, and accelerometer data may be analyzed along with the gaming context. Based on this analysis the game may be modified in various ways including those described earlier. The game may be modified based on a single gamer whose affect has been sensed. An aggregating 650 engine will analyze the sensed affect from the gamer and the other gamers. The aggregating 650 engine can be used to modify the game based on the combined affect sensed from all of the gamers involved. In some embodiments, the aggregating 650 engine may gather other sources of information for aggregation including news feeds, Facebook™ pages, Twitter™, Flickr™, and other social networking and media. The social networking pages related to the gamers may be analyzed during the aggregating. In some embodiments, the game may be modified based on the aggregation of all this information.

Figure 7:
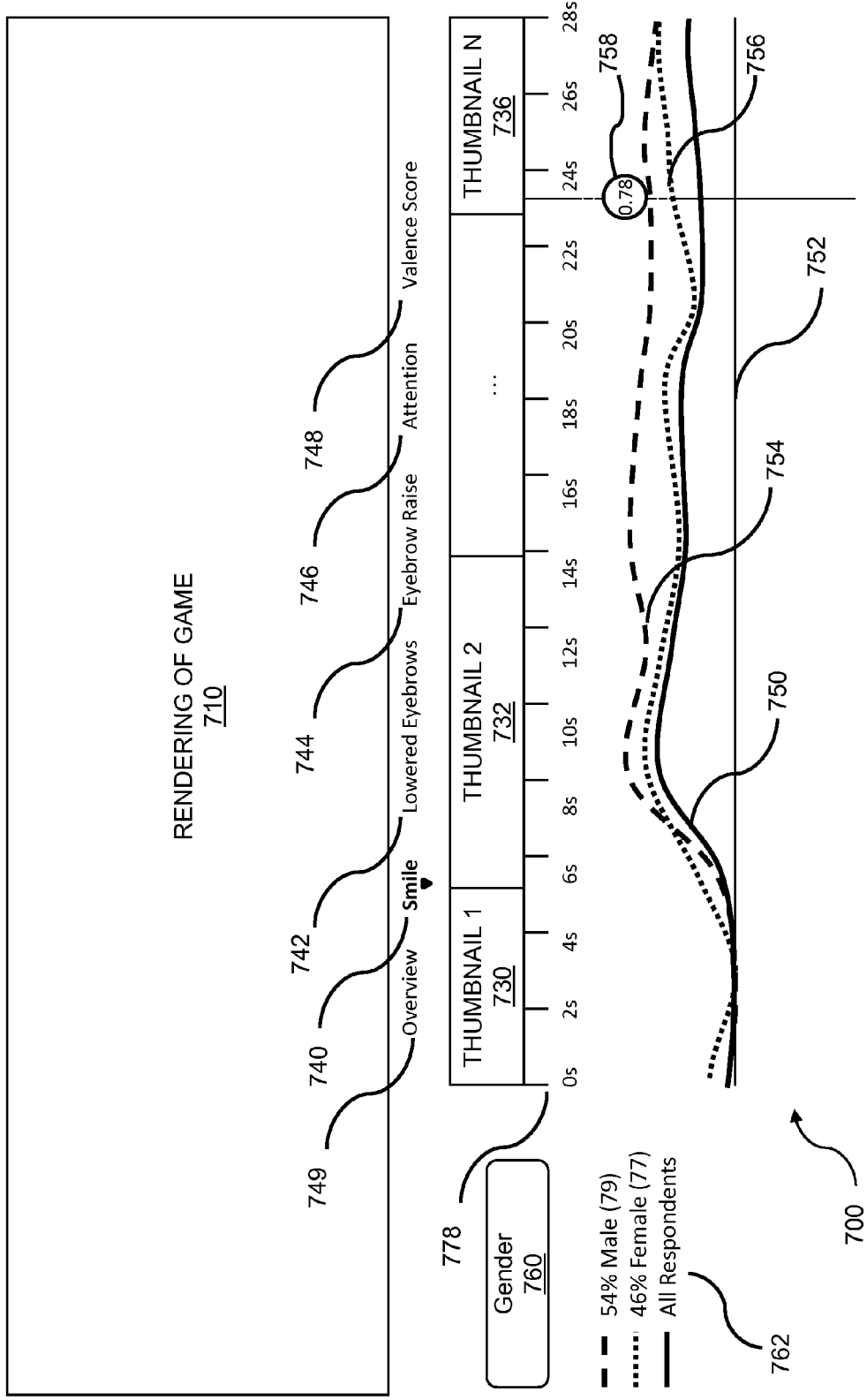
FIG. 7 is a graphical representation of mental state analysis.

FIG. 7 is a graphical representation of mental state analysis that may be shown for gaming analysis and may be presented on an electronic display. The gaming analysis may be used to modify the game and may be used to improve game play. The display may be a television monitor, projector, computer monitor (including a laptop screen, a tablet screen, a net-book screen, and the like), a cell phone display, a mobile device, or other electronic display. An example window 700 is shown which includes, for example, a rendering of a game 710 along with associated mental state information. The visualization may further comprise the rendering related to the game 710. A user may be able to select among a plurality of game renderings using various buttons and/or tabs. The user interface allows a plurality of parameters to be displayed as a function of time, synchronized to the game rendering 710. Various embodiments may have any number of selections available for the user, and some may be other types of renderings instead of video. A set of thumbnail images for the selected rendering, that in the example shown include Thumbnail 1 730, Thumbnail 2 732, through Thumbnail N 736, may be shown below the rendering along with a timeline 778. The thumbnails may show a graphic "storyboard" of the game rendering. This storyboard may assist a user in identifying a particular scene or location within the game rendering. Some embodiments may not include thumbnails, or may have a single thumbnail associated with the rendering, while various embodiments may have thumbnails of equal length while others may have thumbnails of differing lengths. In some embodiments, the start and/or end of the thumbnails may be determined based on changes in the captured gamer mental states associated with the rendering, or may be based on particular points of interest in the game rendering. Thumbnails of one or more gamers may be shown along the timeline 778. The thumbnails of gamers may include peak expressions, expressions at key points in the game rendering 710, etc.

Some embodiments may include the ability for a user to select a particular type of mental state information for display using various buttons or other selection methods. The mental state information may be based on one or more descriptors. The one or more descriptors may include, but are not limited to, one of AU4, AU12 and valence. By way of example, in the window 700, the smile mental state information is shown as the user may have previously selected the Smile button 740. Other types of mental state information that may be available for user selection in various embodiments may include the Lowered Eyebrows button 742, Eyebrow Raise button 744, Attention button 746, Valence Score button 748 or other types of mental state information, depending on the embodiment. An Overview button 749 may be available to allow a user to show graphs of the multiple types of mental state information simultaneously. The mental state information may include probability information for one or more descriptors, and the probabilities for the one of the one or more descriptors may vary for portions of the game rendering.

Because the Smile option 740 has been selected in the example shown, smile graph 750 may be shown against a baseline 752, showing the aggregated smile mental state information of the plurality of individuals from whom mental state data was collected for the game. The male smile graph 754 and the female smile graph 756 may be shown so that the visual representation displays the aggregated mental state information. The mental state information may be based on a demographic basis as those gamers who comprise that demographic react to the game. The various demographic based graphs may be indicated using various line types as shown or may be indicated using color or other method of differentiation. A slider 758 may allow a user to select a particular time of the timeline and show the value of the chosen mental state for that particular time.

Various types of demographic-based mental state information may be selected using the demographic button 760 in some embodiments. Such demographics may include gender, age, race, income level, education, or any other type of demographic including dividing the respondents into those respondents that had higher reactions from those with lower reactions. A graph legend 762 may be displayed indicating the various demographic groups, the line type or color for each group, the percentage of total respondents and/or absolute number of respondents for each group, and/or other information about the demographic groups. The mental state information may be aggregated according to the demographic type selected. Thus, aggregation of the mental state information is performed on a demographic basis so that mental state information is grouped based on the demographic basis, for some embodiments. By way of example, a product or service developer may be interested in observing the mental state of a particular demographic group.

Figure 8:
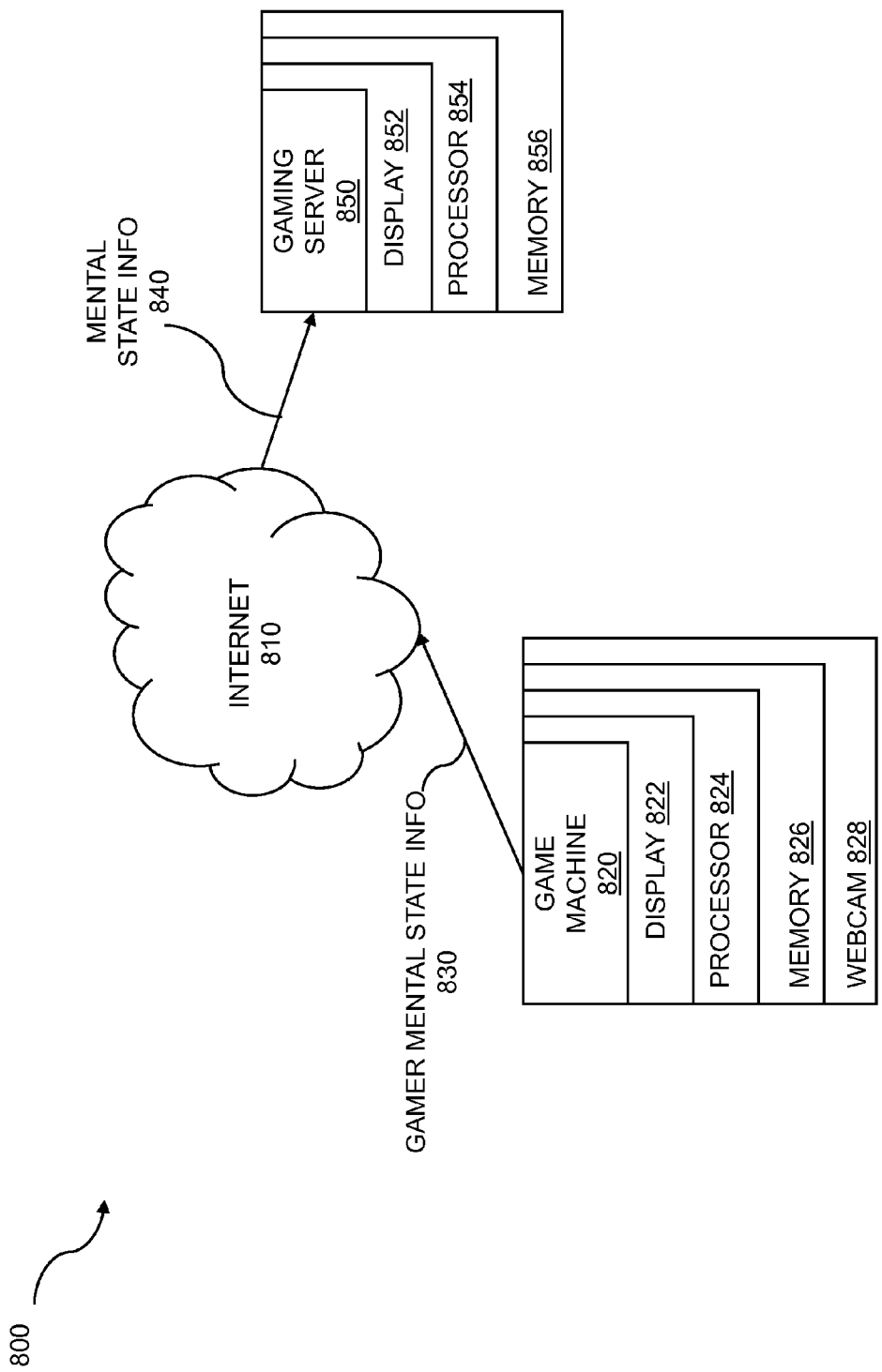
FIG. 8 is a system diagram for evaluating mental states.

FIG. 8 is a system diagram for evaluating mental states. The Internet 810, intranet, or other computer network may be used for communication between or among the various computers involved in gaming. A game machine or client computer 820 has a memory 826 which stores instructions, and one or more processors 824 attached to the memory 826 wherein the one or more processors 824 can execute instructions stored in the memory 826. The memory 826 may be used for storing instructions, for storing mental state data, for system support, gaming information, and the like. The game machine 820 also may have an Internet connection to carry gamer mental state information 830, and a display 822 that may present one or more games. The game machine 820 may be able to collect mental state data from one or more people as they play a game or games. In some embodiments there may be multiple client computers that each collect mental state data from people as they participate in the game. The game machine 820 may have a camera 828, such as a webcam, for capturing an individual's interaction with a game including video of the gamer. The camera 828 may refer to a webcam, a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, and multiple webcams used to capture different views of people who are gaming or any other type of image capture apparatus that may allow image data captured to be used by the electronic system.

As the mental state data is collected, the game machine 820 may upload information to a gaming server 850 or analysis computer, based on the mental state data from the plurality of people who play the game. The game machine 820 may communicate with the gaming server 850 over the Internet 810, intranet, some other computer network, or by any other method suitable for communication between two computers. In some embodiments, parts of the gaming server 850 functionality may be embodied in the client computer.

The gaming server 850 may have a connection to the Internet 810 to enable gaming and mental state information 840 to be received by the gaming server 850. The mental state information 840 may include the gamer mental state information 830 as well as mental state information from other gamers, in some embodiments. Further, the gaming server 850 may have a memory 856 which stores instructions, data, help information and the like, and one or more processors 854 attached to the memory 856 wherein the one or more processors 854 can execute instructions. The gaming server 850 may have a memory 856 which stores instructions and one or more processors 854 attached to the memory 856 wherein the one or more processors 854 can execute instructions. The memory 856 may be used for storing instructions, for storing mental state data, for system support, and the like. The analysis computer may use its Internet, or other computer communication method, to obtain mental state information 840. The gaming server 850 may receive mental state information collected from a plurality of gamers from the game machines 820, and may aggregate mental state information on the plurality of people who play the game.

The gaming server 850 may process mental state data or aggregated mental state data gathered from a person or a plurality of people to produce mental state information about the person or a plurality of people. In some embodiments, the gaming server 850 may obtain mental state information 830 from the game machine 820. In this case the mental state data captured by the game machine 820 was analyzed by the game machine 820 to produce mental state information for uploading.

In some embodiments, the gaming server 850 may receive or analyze to generate aggregated mental state information based on the mental state data from the plurality of people who play the game and may present aggregated mental state information in a rendering on a display 852. In some embodiments, the analysis computer may be set up for receiving mental state data collected from a plurality of people as they play the game, in a real-time or near real-time embodiment. In at least one embodiment, a single computer may incorporate the client, server and analysis functionality. Gamer mental state data may be collected from the game machines 820 to form mental state information on the person or plurality of people playing the game. The system 800 may include a computer program product embodied in a non-transitory computer readable medium for game play.

Each of the above methods may be executed on one or more processors on one or more computer systems. Embodiments may include various forms of distributed computing, client/server computing, and cloud based computing. Further, it will be understood that for each flowchart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, by a computer system, and so on. Any and all of which implementations may be generally referred to herein as a "circuit," "module," or "system."

A programmable apparatus that executes any of the above mentioned computer program products or computer implemented methods may include one or more processors, microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random access memory (RAM), a read-only memory (ROM), an erasable programmable read-only memory (EPROM), Flash, MRAM, FeRAM, phase change memory, an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples, but is to be understood in the broadest sense allowable by law.

What is claimed is:

1. A computer implemented method for gaming comprising:

collecting mental state data, wherein the mental state data includes facial data and physiological data, captured by a webcam, of an individual while the individual is involved in a game;
analyzing, using a web services server, the mental state data to produce mental state information; and
modifying the game based on the mental state information, wherein the modifying the game includes:
changing tasks with which the individual is presented based on a threshold, wherein the threshold comprises a divider in the mental state information that provides for dividing the respondents into those respondents that had higher reactions from those with lower reactions; and
modifying an avatar that represents the individual, wherein the avatar is animated based on the mental state information.

2. The method of claim 1 wherein the collecting mental state data further comprises collecting actigraphy data.

3. The method of claim 1 further comprising inferring mental states with regard to the game based on the mental state data which was collected wherein the mental states include one or more of frustration, confusion, disappointment, hesitation, cognitive overload, focusing, engagement, attention, boredom, exploration, confidence, trust, delight, disgust, skepticism, doubt, satisfaction, excitement, laughter, calmness, stress, and curiosity.

4. The method of claim 1 wherein the game is within an electronic gaming environment.

5. The method of claim 1 wherein the changing tasks includes making the game harder.

6. The method of claim 5 wherein the mental state information includes an indication of boredom.

7. The method of claim 1 wherein the changing tasks includes making the game easier.

8. The method of claim 7 wherein the mental state information includes an indication of frustration.

9. The method of claim 1 wherein the game is a multiplayer game.

10. The method of claim 9 wherein the modifying the game includes modifying an avatar that represents a group of people who are playing the multiplayer game.

11. The method of claim 10 wherein the avatar represents a collective mental state for the group of people.

12. The method of claim 9 wherein the multiplayer game includes requiring players to imitate a face.

13. The method of claim 9 wherein the multiplayer game includes an objective of achieving a collective mental state.

14. The method of claim 9 wherein the multiplayer game includes an objective of avoiding a collective mental state.

15. The method of claim 1 wherein the game includes an objective of achieving a mental state by the individual.

16. The method of claim 1 wherein the game includes an objective of avoiding a mental state by the individual.

17. The method of claim 1 further comprising developing a mental state for a computer generated player.

18. The method of claim 17 wherein the computer generated player is competing against the individual.

19. The method of claim 17 wherein the computer generated player is on a team with the individual.

20. A computer program product stored on a non-transitory computer-readable medium for gaming, the computer program product comprising:
code for collecting facial data and physiological data using a webcam;
code for collecting mental state data, wherein the mental state data includes the facial data of an individual while the individual is involved in a game;

code for analyzing, using a web services server, the mental state data to produce mental state information; and code for modifying the game based on the mental state information, wherein the modifying the game includes:

changing tasks with which the individual is presented based on a threshold, wherein the threshold comprises a divider in the mental state information that provides for dividing the respondents into those respondents that had higher reactions from those with lower reactions; and modifying an avatar that represents the individual, wherein the avatar is animated based on the mental state information.

21. A computer system for gaming comprising:

a memory for storing instructions;

one or more processors attached to the memory wherein the one or more processors are configured to:

collect facial data and physiological data using a webcam;

collect mental state data, wherein the mental state data includes the facial data of an individual while the individual is involved in a game;

analyze, using a web services server, the mental state data to produce mental state information; and modify the game based on the mental state information; wherein modification of the game includes:

changing tasks with which the individual is presented based on a threshold, wherein the threshold comprises a divider in the mental state information that provides for dividing the respondents into those respondents that had higher reactions from those with lower reactions; and modifying an avatar that represents the individual, wherein the avatar is animated based on the mental state information.

22. The method of claim 1 wherein the webcam comprises a video camera, a still camera, a thermal imager, a CCD device, a phone camera, or a three-dimensional camera.

23. The method of claim 9 further comprising sharing the mental state information across a social network.

24. The method of claim 23 wherein the sharing is used in rating for games and where the sharing includes information on affect that indicates a level of engagement.

25. The method of claim 23 wherein the sharing is real time and a gaming experience is modified in real time.

26. The method of claim 23 wherein the sharing further comprises sharing modified mental state information which is more positive than inferred mental states as analyzed.

27. The method of claim 9 wherein the mental state information includes mental state information from the other players of the multiplayer game.

28. The method of claim 27 further comprising aggregating the mental state information on a plurality of people who play the multiplayer game.

29. The method of claim 28 wherein the aggregated mental state information is rendered on a display.

* * * * *